United States Patent [19]

Diss

[11] 4,055,088
[45] Oct. 25, 1977

[54] APPARATUS FOR SAMPLING DRY SOLIDS

[75] Inventor: Edward M. Diss, Midland, Mich.

[73] Assignee: The Dow Chemical Company, Midland, Mich.

[21] Appl. No.: 729,328

[22] Filed: Oct. 4, 1976

[51] Int. Cl.² .............................................. G01N 1/20
[52] U.S. Cl. .................................................... 73/424
[58] Field of Search .................. 73/421 B, 423 R, 424

[56] References Cited
U.S. PATENT DOCUMENTS

| 3,585,864 | 6/1971 | Dellyes | 73/424 |
| 3,751,991 | 8/1973 | Fisher | 73/424 |

FOREIGN PATENT DOCUMENTS

| 212,619 | 4/1968 | U.S.S.R. | 73/424 |

Primary Examiner—S. Clement Swisher
Attorney, Agent, or Firm—V. Dean Clausen

[57] ABSTRACT

In packaging certain dry, free-flowing solid materials, the packaging operation involves delivering the solids from a classifier screen to a storage hopper through an inclined conduit. Within the conduit the particles tend to segregate into distinct layers, such that each layer contains solids of a different size. In this situation it is difficult to obtain a representative sample of the product being packaged, for quality control purposes. The present invention solves the problem with a sample receiving and collection conduit inside the hopper, which is operated by an oscillator means and timer mechanism. The timed oscillation of the receiving and collection conduit permits a periodic collection of the entire solids stream as it flows from the inclined conduit into the hopper.

5 Claims, 2 Drawing Figures

APPARATUS FOR SAMPLING DRY SOLIDS

BACKGROUND OF THE INVENTION

Broadly, the invention relates to an apparatus for collecting samples of solid particles. More specifically, the apparatus is useful for sampling a stream of dry, free-flowing solids at a point between a classifier means and a packaging means.

Many chemical products are marketed in the form of dry, solid particles. An example of products in this category are ion exchange resins, which are used in home water conditioners to remove metal ions from the water. A commercially available ion exchange resin in marketed in the form of dry, solid, free flowing beads which range in size from about 20 mesh to 50 mesh.

In a typical manufacturing process the resin beads are discharged from a holding vessel onto a classifier screen. On the classifier screen the beads are separated into three general size ranges, for example, oversize beads undersize beads, and product size beads. From the classifier screen the product size beads are directed through a downwardly inclined delivery conduit and they drop into a hopper through an opening in the top of the hopper. When the hopper fills to a certain point, the solids are removed through a bottom opening and discharged into packaging containers.

To insure that the resin beads which make up the product are in the desired size range, it is necessary to periodically sample the solids being delivered into the hopper. Referring to the system described above, as the resin beads are carried into the storage hopper through the downwardly inclined conduit, the beads tend to segregate within the conduit. When segregation occurs, the larger (more dense) solids work toward the center of the material stream, and the smaller (less dense) solids will work outwardly and move along the periphery of the material stream. Because of this segregation problem, it is difficult to obtain a representative sample of the resin beads which are collected in the storage hopper. It is desirable, therefore, to collect a sample from the material stream at a point somewhere within the delivery conduit. In addition to collecting the sample in the delivery conduit, the sampling device must be capable of obtaining a full section of the material stream. Otherwise, the "product cut" will not represent the full size range of the particles being delivered into the storage hopper.

The conventional grabber type sampling devices are usually not satisfactory for this purpose. One reason is that there may be a limited amount of space between the classifier means and the top opening in the storage hopper. This creates a problem, in that the sample must be moved laterally from the point at which it is collected in the delivery conduit to a point at which it can be picked up. The lateral transfer of the sample, therefore, usually requires several pieces of equipment. This is undesirable from the standpoint of cost and the number of moving parts which are involved.

SUMMARY OF THE INVENTION

An apparatus is provided for sampling a stream of dry, free-flowing solids. In a specific embodiment, the sample is obtained at a point between a means for classifying the solids and a means for packaging the solids. The apparatus includes a hopper suitable for storing the solids, which has a top wall with a central opening therein. From the classifier means the solids are carried into the hopper through a delivery conduit which connects into the top wall opening. Positioned inside the hopper is a sample receiving conduit.

The sample receiving conduit is a two-piece unit, which includes an upper conduit section and a lower conduit section, which are coupled together. The upper end of the upper conduit section is an open end, which in normal position is below the top wall opening of the hopper. The lower conduit section has a lower end, which extends outside the storage hopper, and which connects into a collection conduit. At a point above the collection conduit an oscillator means is fastened to the lower conduit section of the sample receiving conduit.

During a sampling operation the oscillator means rotates the sample receiving conduit between two positions. In the first position, the open upper end of the sample receiving conduit is brought into direct alignment with the top wall opening of the storage hopper. In this position the solids can be received by the sample receiving conduit. Once the sample has been obtained, the oscillator rotates the sample receiving conduit to a second position, in which the open upper end is not in alignment with the opening of the hopper. The lower conduit section of the sample receiving conduit is enclosed by a support column. In turn, the support column is fastened to an inside wall surface of the hopper. A bearing assembly is fitted to the sample receiving conduit near the point at which the upper conduit section is coupled to the lower conduit section.

DESCRIPTION OF A PREFERRED EMBODIMENT

Figure 1:
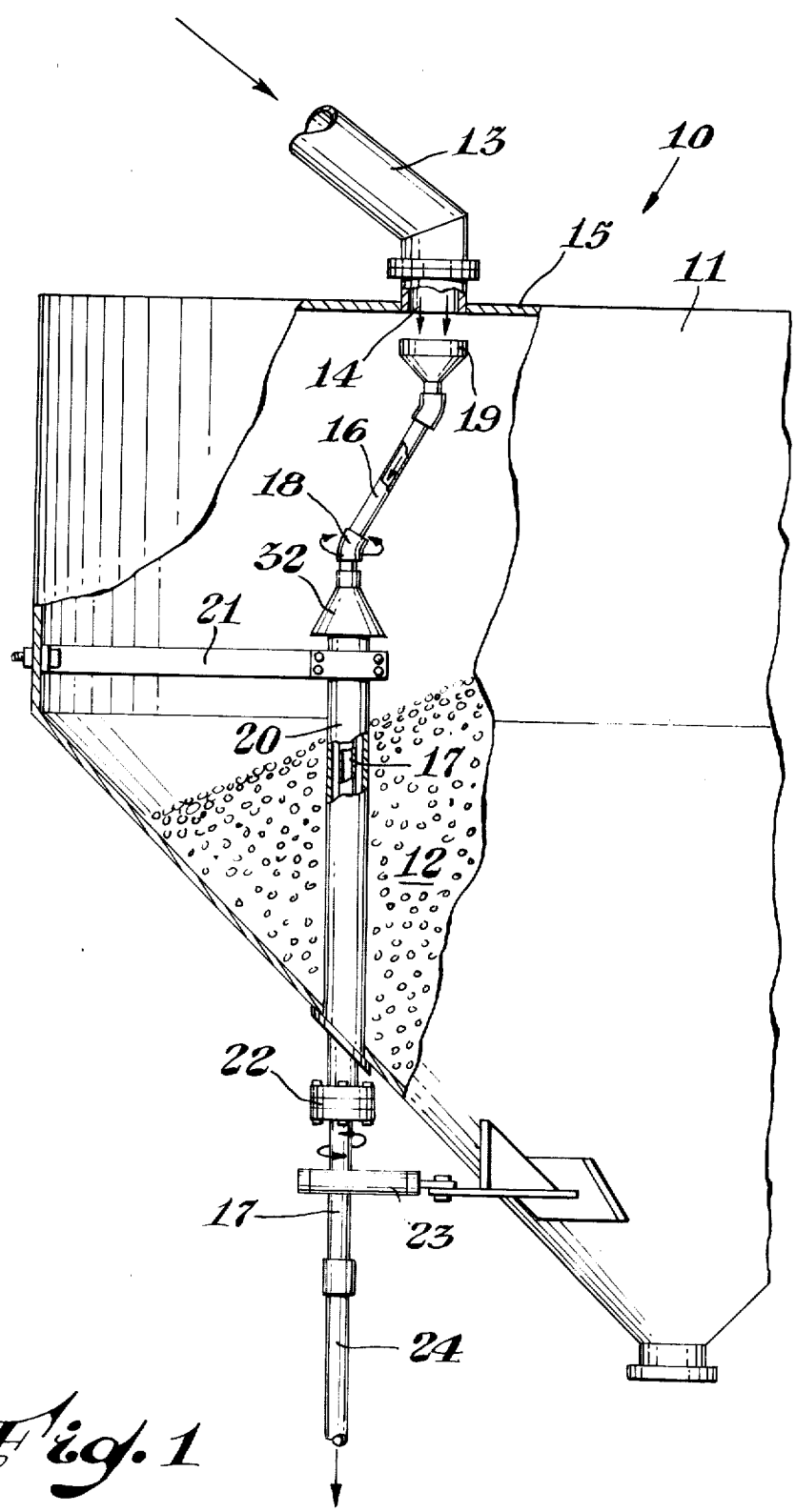
FIG. 1 is a front view, partly in section, of one embodiment of the sampling apparatus of this invention.

Referring to the drawing, the sampling apparatus shown in FIG. 1 is indicated generally by numeral 10. The apparatus 10 includes a hopper 11 which is suitable for storing dry, free-flowing solid particles, as indicated by numeral 12. The lower end of a delivery conduit 13 connects into the hopper 11 at opening 14 in the top wall 15 of the hopper. The opposite end of conduit 13 (the upper end) communicates with a classifier screen for classifying the particles 12. The upper end of conduit 13 and the classifier screen are not shown in the drawing.

Positioned inside of hopper 11 is a sample receiving conduit. The sample receiving conduit, as a two piece unit, is made up of an upper conduit section 16 and a lower conduit section 17. These conduit sections are joined together by a coupling 18. The open upper end of conduit section 16 is defined by a funnel-shaped opening 19. When the sample receiving conduit is in operating position, the funnel-shaped end 19 is positioned inside hopper 11 at a point just below the opening 14. The lower end of conduit section 17 extends outside the hopper 11, as indicated in FIG. 1.

Support for the sample receiving conduit is provided by a column 20, which encloses the lower conduit section 17. In turn, the column 20 is fastened to the inside wall surface of hopper 11 by a support strap 21. At the lower end column 20 is coupled to the conduit section 17 by a bearing assembly 22. In addition, an air cylinder 23 is attached to the lower conduit section 17 just below the bearing assembly 22. The air cylinder 23 provides means for oscillating the sample receiving conduit between a position for receiving the sample and a position in which the sample is not received by the conduit. The air cylinder is operated by a solenoid valve which, in turn, is controlled by a timer mechanism. The solenoid valve and timer mechanism are not shown in the drawing.

Figure 2:
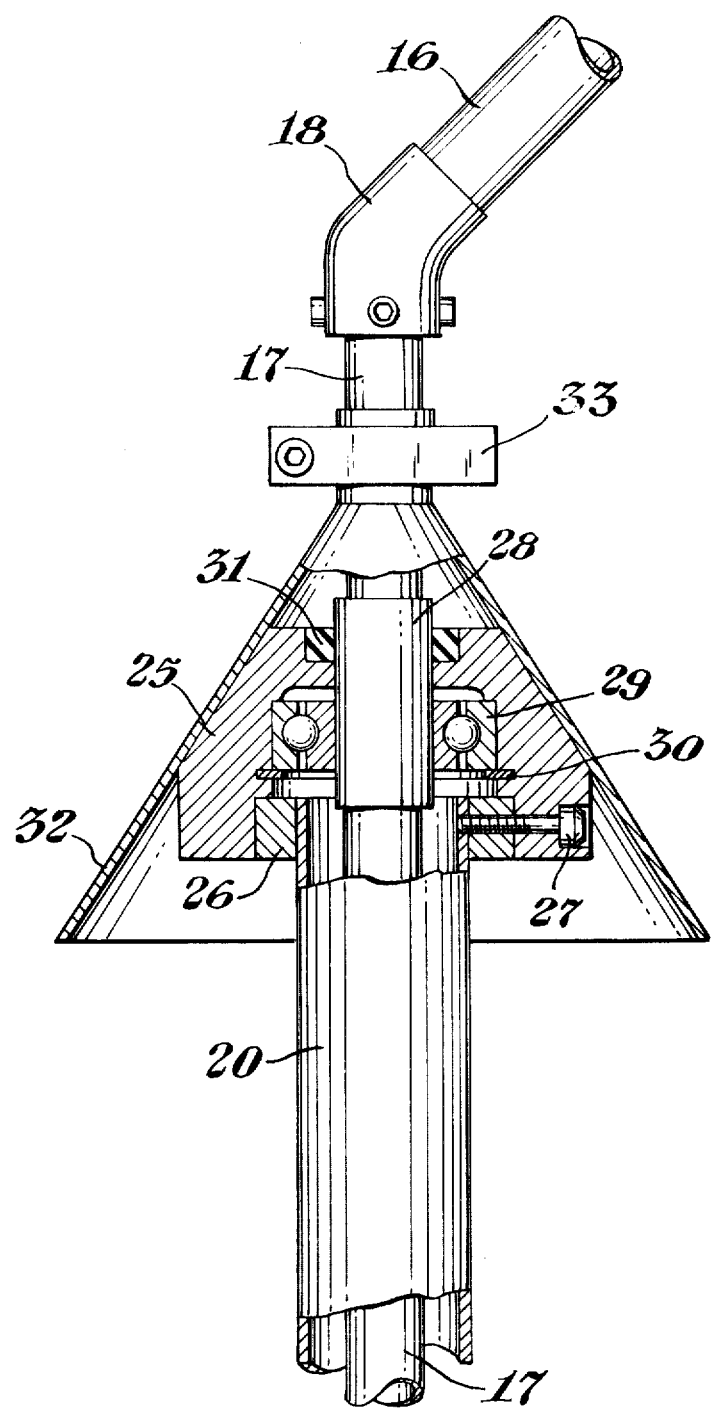
FIG. 2 is a detail view of one part of the sample receiving conduit, as included in the apparatus illustrated in FIG. 1.

A collection conduit 24 is connected into the conduit section 17 just below the point at which the air cylinder 23 fastens to the conduit section. Referring particularly to FIG. 2, the upper end of support column 20 is joined to the conduit section 17 by a second bearing assembly. This bearing assembly includes a bearing block 25, which seats on a collar 26. In turn, the bearing block and the collar are fastened to column 20 by several cap screws. Only one cap screw is shown in the drawing, as indicated by numeral 27.

A bushing 28 is fitted over the upper end of conduit section 17. The purpose of the bushing is to enlarge the diameter of the conduit section to fit a conventional size ball bearing 29. Bearing 29 is retained in the bearing block 25 by a snap ring 30. Above the bearing 29 a seal ring 31 is fitted between the bearing block and bushing 28. A cone-shaped shield 32 is fastened to the conduit section 17 above the bearing assembly by a split collar 33. As indicated in FIG. 2, the shield 32 fits down against the sloping outer surface of bearing block 25. The contact of the shield with the bearing block is a slide fit which allows the shield to rotate along with the conduit section 17.

To illustrate the practice of this invention, a typical operation of the sampling apparatus 10 will now be described. For the purpose of this description, assume that the solids to be sampled comprise ion exchange resin beads, as described earlier in this specification. The "product cut" consists of dry, solid, free-flowing particles 12, which range in size from about 20 mesh to 50 mesh. As described earlier, the product cut is delivered from the classifier screen (not shown) into the storage hopper 11 through the delivery conduit 13.

When it is desired to obtain a sample of the product, the air cylinder 23 will rotate the sample receiving conduit to the receiving position. At the receiving position, the funnel-shaped opening 19 will be in direct alignment with the opening 14 in the top wall 15 of hopper 11. By centering the opening 19 with opening 14, the full stream of solids in conduit 13 can carry down through the conduit sections 16 and 17 and into the collection conduit 24. At the opposite end of conduit 24 (not shown in the drawing) the solids sample is collected in a container. As part of the quality control procedure, the sample is then checked to determine particle size distribution, and other properties relating to quality control.

The usual procedure is to take a solid sample about every 20 minutes. For each sample collection, the sample receiving conduit is allowed to remain in the receiving position for about 1 second. The timing of the sample collection is achieved by appropriate adjustment of the timer mechanism and the solenoid valve which controls the air cylinder 23. At the end of each 1 second sampling period, the air cylinder rotates the sample receiving conduit to a position in which the funnel shaped opening 19 is not aligned with the opening 14 in hopper 11. In the non-receiving position, therefore, the solids fall directly from conduit 13 into hopper 11.

There are certain features of the sampling apparatus of this invention which are not found in the commercially available sampling devices. One feature is that the present sampling device is of a relatively simple construction, which can operate in a limited amount of space. Another important feature is found in the procedure for collecting the sample. As explained earlier, if conventional grabber type samplers are used, the sample must be moved laterally, by a mechanical transfer, from the delivery conduit to a pick-up point. By contrast, in the present sampling apparatus, there is no requirement to collect the sample from the delivery conduit. Instead, the sample stream passes directly from the delivery conduit and straight downwardly through the sample receiving conduit, by gravity flow, into a collection point.

Another feature of this apparatus is a protective shield for the inside bearing assembly on the sample receiving conduit. In a normal operation the solids 12 will usually reach a level in hopper 11 which is above the bearing assembly at the upper end of conduit section 17. At this level it is possible for the solids to work into the bearing assembly and actually damage the bearing race by abrasion. In the present apparatus the shield 32 prevents the particles from working into the bearing assembly from any direction. Although the shield 32 flares outwardly to define an open bottom, the particles 12 will not work upwardly into the bearing assembly. The reason for this is that the angle of repose, as defined by the surface layer of the solids 12, is oriented in a downward plane.

The invention claimed is:

1. An apparatus for sampling a stream of dry, free-flowing solids at a point between a classifier means and a packaging means, the apparatus including:
   a hopper which is suitable for storing dry, free-flowing, solids, and which includes a top wall with an opening therein;
   a delivery conduit which communicates with a means for classifying the dry solids and with the top wall opening, and which is suitable for carrying a stream of the dry solids from the classifier means to the storage hopper;
   a sample receiving conduit which includes an upper section and a lower section which is coupled to the upper section;
   the upper section of the sample receiving conduit having an open end which is positioned inside the storage hopper below the opening in the top wall;
   the lower section of the sample receiving conduit having a lower end which extends outside the storage hopper;
   a collection conduit which connects into the said lower end of the sample receiving conduit;
   an oscillator means which is fastened to the said lower end of the sample receiving conduit, the oscillator being adapted for moving the sample receiving conduit to a first position in which the open end of the upper section is in direct alignment with the opening in the top wall of the hopper, and a second position in which the said open end is not aligned with the opening in the top wall of the hopper;
   a support column which is positioned inside the hopper, which is fastened to the hopper, and which encloses the lower section of the sample receiving conduit;
   a bearing assembly which is fitted to the lower section of the sample receiving conduit near the point at which the said lower section is coupled to the upper section of the sample receiving conduit.

2. The apparatus of claim 1 in which the open end of the upper section of the sample receiving conduit is a funnel-shaped opening.

3. The apparatus of claim 1 which includes a shield member, the shield being positioned inside the hopper, and the shield enclosing the bearing assembly.

4. The apparatus of claim 3 in which the shield member is a cone-shaped member.

5. The apparatus of claim 1 in which the oscillator means is an air cylinder.

* * * * *